United States Patent [19]

Ashinoff

[11] Patent Number: 5,240,413
[45] Date of Patent: Aug. 31, 1993

[54] DECORATIVE ORTHODONTIC BRACE AND METHOD

[76] Inventor: Leslie A. Ashinoff, 1670 Cynron La., East Meadow, N.Y. 11554

[21] Appl. No.: 10,832

[22] Filed: Jan. 29, 1993

[51] Int. Cl.5 ................................. A61C 3/00
[52] U.S. Cl. ........................ 433/24; 433/2; 433/22
[58] Field of Search ............... 433/2, 8, 9, 20, 22, 433/24

[56] References Cited

U.S. PATENT DOCUMENTS

| | | | |
|---|---|---|---|
| 4,527,975 | 7/1985 | Ghafari et al. | 433/8 |
| 4,585,413 | 4/1986 | Wool | 433/8 |
| 5,160,260 | 11/1992 | Chang | 433/8 |

*Primary Examiner*—Cary E. O'Connor

[57] ABSTRACT

A decorative mouth brace, i.e. orthodontic construction, in which the tooth-repositioning wires in spanning relation between brackets are adorned with decorative objects, such as charms or the like, to enhance the heretofore unsightly appearance of this object.

1 Claim, 1 Drawing Sheet

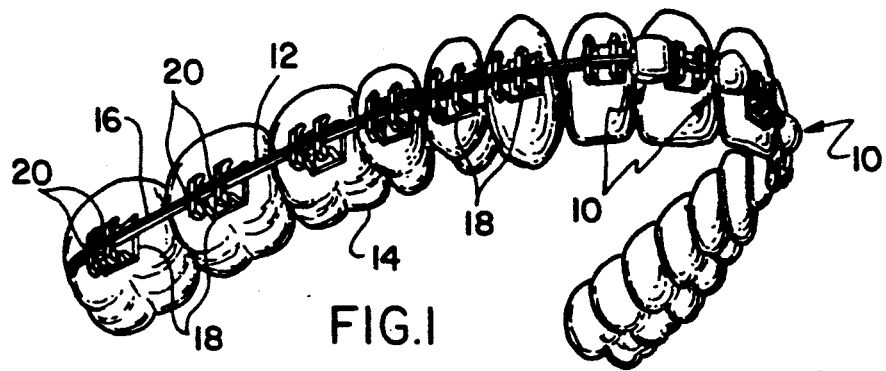
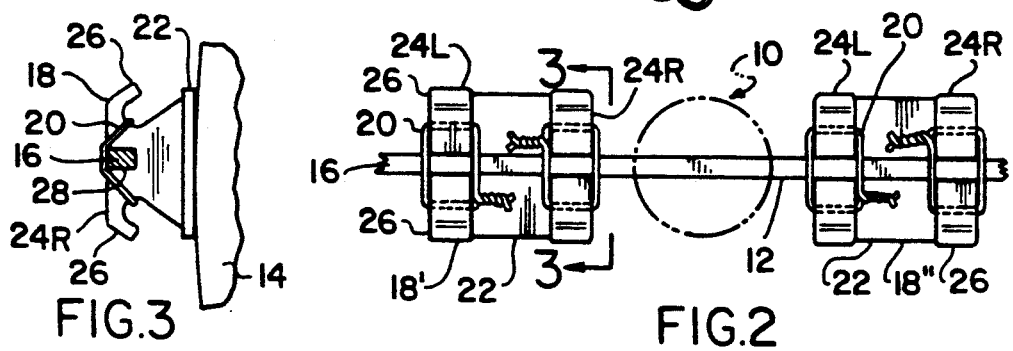
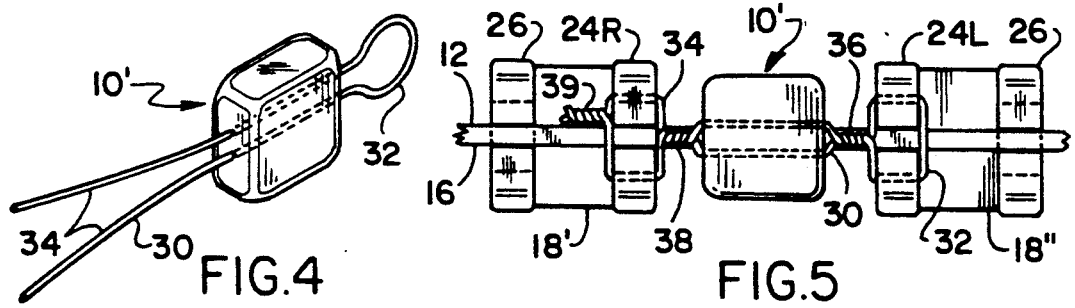
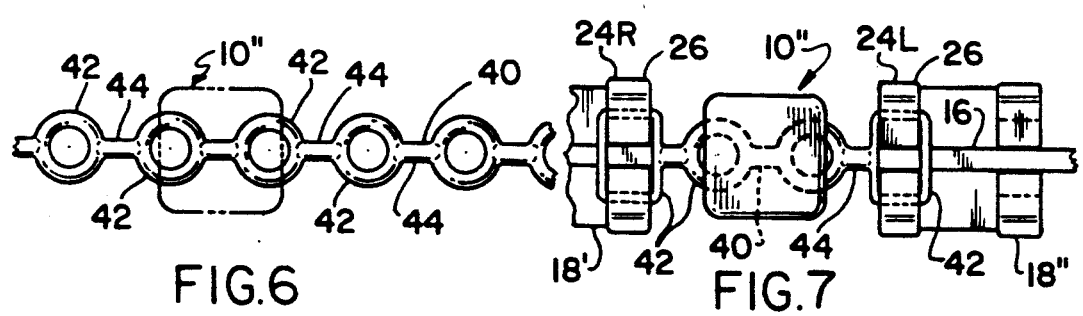
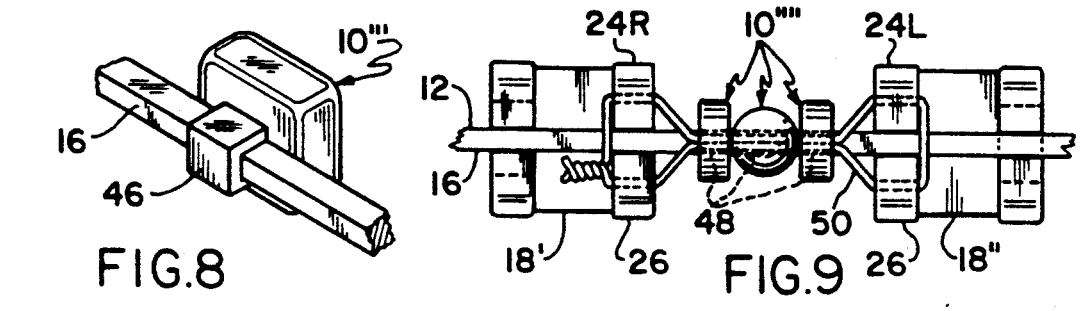

DECORATIVE ORTHODONTIC BRACE AND METHOD

The present invention relates generally to providing a decorative appearance to an orthodontic brace which heretofore, because constructed of brackets and wires is aptly characterized as unsightly, and more particularly relates to achieving this enhancement in appearance while maintaining intact the function of the brace in relocating improperly located teeth.

EXAMPLES OF THE PRIOR ART

Traditionally an orthodontic brace is attached to the front or labial side of the patient's teeth which is the obviously preferred location for obviating irritation to the patient's tongue. However, the unsightliness of the brace, consisting as it does of brackets and wires, has contributed to efforts to relocate the brace to the hidden or lingual side of the patient's teeth, as described and illustrated in U.S. Pat. Nos. 4,107,844 and 4,386,908 issued to Craven H. Kurz, even though this is a less desirable location for the already noted and other reasons.

Broadly, it is an object of the present invention to provide an orthodontic brace overcoming the foregoing and other shortcomings of the prior art.

More specifically, it is an object to attach appearance-enhancing objects to the structural components of the brace without interfering with the orthodontic functioning of these components.

One such component to be noted is the brace arch wire which, as understood, is what is used to apply torque and forces which relocate the improperly positioned teeth. This wire and its supporting brackets are in prominent display and significantly contribute to the unsightliness of the brace. Underlying the present invention, however, is the recognition that the arch wire is, for dental or teeth position-shifting purposes, in a clearance position spaced forwardly of the teeth. In accordance with the present invention, the arch wire operative clearance position is thus used to advantage to support charm-like display objects, in that the thickness of the display object rearwardly of its central plane is readily accommodated in the clearance existing between the wire and the front of labial surface of the teeth, while the front thickness or portion of the display object is prominently displayed as foreground to the background teeth of the mouth display presented to a viewer in facing relation to a patient "wearing" a brace, all to the end of significantly enhancing the appearance of the brace, as will be explained subsequently in greater detail.

The description of the invention which follows, together with the accompanying drawings, should not be construed as limiting the invention to the examples shown and described, because those skilled in the art to which this invention appertains will be able to devise other forms thereof within the ambit of the appended claims.

FIG. 1 is a perspective view on an enlarged scale of a patient's upper dentition embodying display objects according to the present invention as part of a traditional orthodontic brace;

FIG. 2 is a detailed front elevational view of adjacent orthodontic brackets of the orthodontic brace of FIG. 1;

FIG. 3 is a cross sectional view as taken along line 3—3 of FIG. 2;

FIG. 4 is an isolated perspective view of a first mounting embodiment for the charm display objects of the present invention;

FIG. 5 is a front elevational view showing mounting details of the installed display object of FIG. 4;

FIG. 6 is a front elevational view of an alternative support for a charm display object of the present invention;

FIG. 7 is a front elevational view showing mounting details of the installed display object of FIG. 6;

FIG. 8 is a rear perspective view of still another third mounting embodiment for display objects according to the present invention; and FIG. 9 is a front elevational view of a fourth mounting embodiment for display objects according to the present invention.

The present invention relates to enhancing the appearance or display of an orthodontic brace which heretofore could aptly be characterized as unsightly To this end, and as will be explained in greater detail subsequently, use is made of display objects 10, which by virtue of shape, color and other such attributes, function much like bracelet charms, but in an orthodontic brace setting, to enhance the appearance of the brace 12, all as is generally shown in FIG. 1. That is, in FIG. 1 is shown plural charm-like display objects 10 attached to a conventional orthodontic dental brace 12 which in turn is mounted on a patient's in-place upper denture 14. As understood, brace 12 consists of an arch wire 16 of a selected length which is supported on an array of spaced-apart brackets 18 and secured in place with stainless steel wire typically 0.010 inches in diameter. Brackets 18 are bonded to the labial surface of teeth 14 with suitable cement after surface etching. In use, typically over a period of up to three years, periodic adjustments in the tautness and other mounting conditions of wire 16 are made by the orthodontist to correspondingly transmit torque, thrust and other like forces on specific teeth to shift these teeth to more desirable permanent positions.

In the past, wearing braces was regarded as undesirable and considered to detract from the wearer's appearance. However, the concept of the present invention is to encourage the wearer to be proud that he/she is participating in a corrective dental practice and show off that they are doing so. Thus, the present invention provides an implementation of this concept by allowing the patient to decorate the brace 12 and, in doing so, enhance the appearance thereof.

Underlying the present invention is the recognition that the wire 16 for dental or teeth position-shifting purposes, occupies a clearance position spaced forwardly of the teeth 14, and this wire position is accordingly used to advantage as a support for the dental charm-like display objects 10. Each display object 10 must, of necessity, have a thickness and, thus, in a preferred mounting embodiment in which the wire is threaded through the central plane of the display object 10, the thickness of the display object rearwardly of the central plane is readily accommodated in the clearance existing between the wire 16 and the front or labial surface of the teeth 14, while the front thickness or portion of the display object 10 is prominently displayed as foreground to the background teeth of the mouth display presented to a viewer in facing relation to a patient "wearing" a brace 12.

In FIGS. 2 and 3, to which figures reference should now be made, details of a pair of brackets 18 and arch wire 16 are shown as assembled components of a brace 12. Brackets 18' and 18" will be understood to be any selected two of the brackets 18 that are typically applied to the anterior teeth 14. Display object or device 10 is shown in phantom line perspective as being located between brackets 18' and 18" and secured in any one of several ways now to be described. Object 10 can be made of any material that is compatible for use in the mouth and is of sufficient strength for this purpose. It also is intended to be made in any specific shape (e.g. heart, diamond, half moon, etc.) and of a size to fit in an interposed position between adjacent brackets 18' and 18".

As best seen in FIG. 1, each bracket 18 has a base member 22, adhered to a tooth 14, a left side T-shaped tab or, in dental parlance, a so-called wing 24L and a right side T-shaped wing 24R. Each of the wings 24 constructionwise include an upper and lower hook member 26. A suitable slot 28 to receive arch wire 16 is arranged on each wing face. Ligature wire 20 is subsequently used to secure arch wire 16 to a cooperating bracket 18, as seen best in FIG. 3.

In a first mounting embodiment that in practice is effective for the purposes intended, charm 10', as shown in FIGS. 4 and 5, is made integral with a length of wire 30 that may be substituted for the FIG. 1 ligature wire 20 on wing 24L of bracket 18" and on wing 24R of bracket 18'. To one side of the charm 10' a loop 32 has been shaped into wire 30 and to the other side a pair of wire legs 34 are left extended and initially unattached. At installation (see FIG. 5) loop 32 is placed about wing 24L and twisted, as at 36. Legs 34 are then twisted at 38, brought about wing 24R and twisted again at 39. Excess wire beyond twist 39 is then trimmed off. Loop 32 and legs 34 thus serve the dual purpose of supporting charm 10' and of substituting for the usual ligature wire 20 that is usually used to secure arch wire 16 to the spaced-apart brackets 18.

Not shown, but readily comprehended is a mounting prepared for charm 10' which is made integral with two lengths of wire 30 extending from opposite sides of the charm and thus forming two groups of legs 34 symmetrical to the charm which in practice are attached to wings 24L, 24R on adjacent cooperating respective brackets 18' and 18".

In a second optional mounting embodiment, advantage is taken of what is known as a power chain 40, as seen in FIG. 6. Chain 40 is manufactured with interconnected loops 42 in continuous lengths and cut to size when used. Chain 40 is made of highly elastic rubber construction material or the like, and is generally applied to adjacent spaced apart brackets to create a tension force therebetween. Each chain loop 40 is connected to an adjacent chain loop by a link 44.

When used with charm 10", chain 40 becomes the support for charm 10". That is, chain 40 is preassembled with charm 10", is trimmed to a convenient length, and looped about bracket wings 24L and 24R of brackets 18' and 18" respectively, as best shown in FIG. 7.

With suitable tweezers, and using a mirror and average dexterity, the patient is able to remove this type of chain charm, and replace it with another. Care need only be taken to avoid unwanted stresses that tend to defeat the position-shifting objective of the orthodontic procedure.

In a third procedure to mount a charm 10 on brace 12, a collar bracket 46 is assembled to the rear face of charm 10''', as best seen in FIG. 8. Bracket 46 is appropriately sized or dimensioned to be compatible with arch wire 16. In use, a number of intended-to-be displayed charms 10''' are threaded along arch wire 16 before the wire is mounted on brackets 18. At the time of the mounting, the supported charms 10''' are manually urged through sliding movement along wire 16 into positions between brackets 18' and 18", during which the wire effectively serves to track the charms during this movement. Once arranged relative to arch wire 16 and brackets 18, brackets 46 can be crimped or swaged on wire 16 to retain the locations of charms 10''' thereon. This type mounting for one or more of the described charms 10''' can remain on wire 16 as orthodontic adjustments are made from time to time.

In FIG. 9 a fourth approach to orthodontic brace decoration is shown in the specific form of a bead arrangement, wherein charms 10'''' are made with a wire-stringing hole 48 therethrough. Various selected shapes, sizes and colors can be featured in the display objects 10 secured on a length of ligature wire 50 which is tied to bracket wings 24L and 24R.

The herein described decorative displays for adorning an orthodontic brace 12 are but a sample of the number of possibilities. For example, the various mounting methods can be used in combination. Additionally, the display objects or charms 10 can be made with lettering thereon and oriented to spell short words or display initials. Colors can be selected according to one's school, favorite team or the like. Charms 10 can also be made of precious metal and in jewelry grade construction material to be lasting in nature and kept as sentimental keepsakes when the brace is removed.

While the components for achieving the within inventive decorative orthodontic brace and the method of constructing same herein shown and disclosed in detail are fully capable of attaining the objectives and providing the advantages hereinbefore stated, it is to be understood that they are merely illustrative of presently preferred embodiments of the invention, and that no limitations are intended to the detail of construction or design herein shown other than as defined in the appended claims.

What is claimed is:

1. A method of decorating an orthodontic brace comprising the steps of constructing an orthodontic brace on a denitture using spaced-apart brackets with projecting tabs, stringing a wire through a stringing opening of a display object, and tying said wire at locations on opposite sides of said display object to cooperating tabs, whereby the presence and the tracking of said display object on said wire enhances the appearance of said brace.

* * * * *